(12) United States Patent
Gerlach (10) Patent No.: US 12,419,737 B2
(45) Date of Patent: Sep. 23, 2025

(54) OPHTHALMOLOGICAL IMPLANT AND METHOD FOR PRODUCING SAME

(71) Applicant: Carl Zeiss Meditec AG, Jena (DE)

(72) Inventor: Mario Gerlach, Glienicke-Nordbahn (DE)

(73) Assignee: Carl Zeiss Meditec AG, Jena (DE)

( * ) Notice: Subject to any disclaimer, the term of this patent is extended or adjusted under 35 U.S.C. 154(b) by 982 days.

(21) Appl. No.: 17/610,639

(22) PCT Filed: May 13, 2020

(86) PCT No.: PCT/EP2020/063332
§ 371 (c)(1),
(2) Date: Nov. 11, 2021

(87) PCT Pub. No.: WO2020/229540
PCT Pub. Date: Nov. 19, 2020

(65) Prior Publication Data
US 2022/0233303 A1      Jul. 28, 2022

(30) Foreign Application Priority Data

May 16, 2019   (DE) ...................... 10 2019 207 175.9

(51) Int. Cl.
*A61F 2/16*        (2006.01)
*G16H 10/60*        (2018.01)

(52) U.S. Cl.
CPC .......... *A61F 2/1613* (2013.01); *G16H 10/60* (2018.01); *A61F 2/16* (2013.01);
(Continued)

(58) Field of Classification Search
CPC ................ A61F 2/16; A61F 2002/1681; A61F 2250/0086; A61F 2250/0089
See application file for complete search history.

(56) References Cited

U.S. PATENT DOCUMENTS

| 6,098,892 A | 8/2000 | Peoples, Jr. |
| 8,812,125 B2 | 8/2014 | Kaula et al. |

(Continued)

FOREIGN PATENT DOCUMENTS

| CN | 107072816 A | 8/2017 |
| DE | 69518865 T2 | 2/2001 |

(Continued)

OTHER PUBLICATIONS

International Search Report for PCT/EP2020/063332, mailed Sep. 10, 2020, 3 pages.

(Continued)

*Primary Examiner* — Bruce E Snow
(74) *Attorney, Agent, or Firm* — DeWitt LLP (57) ABSTRACT

An ophthalmological implant including an imaging optical element, and a haptic with a haptic root. Also, a corresponding method for producing an ophthalmological implant and a characterization system for identifying an ophthalmological implant for example an intraocular lens. The implant includes an unambiguous label and hence an unambiguous and reliable identification option. The label is not able to be mixed-up and is possible with minimal additional technical outlay. The implant includes a rotationally symmetric structural code of identification data of the ophthalmological implant arranged on the haptic root and/or the region of the haptic proximate the haptic root. Also, a method for producing an ophthalmological implant, in which the implant receives, directly during or after the forming, a rotationally symmetric structural code of identification data.

13 Claims, 3 Drawing Sheets

(52) U.S. Cl.
CPC .. *A61F 2002/1681* (2013.01); *A61F 2240/001* (2013.01); *A61F 2250/0086* (2013.01); *A61F 2250/0089* (2013.01); *A61F 2250/0098* (2013.01)

(56) References Cited

U.S. PATENT DOCUMENTS

| | | | |
|---|---|---|---|
| 9,517,126 B2 * | 12/2016 | Wiechmann | A61F 2/14 |
| 11,622,849 B2 * | 4/2023 | Gengler | A61F 2/16 |
| | | | 623/6.17 |
| 2003/0001016 A1 * | 1/2003 | Fraier | G06F 16/9554 |
| | | | 235/462.03 |
| 2006/0001828 A1 * | 1/2006 | Duggan | G02C 7/021 |
| | | | 351/159.69 |
| 2014/0214047 A1 | 7/2014 | Sunalp et al. | |

FOREIGN PATENT DOCUMENTS

| | | |
|---|---|---|
| DE | 10 2008 017 592 A1 | 10/2009 |
| DE | 10 2009 056 810 A1 | 6/2011 |
| EP | 1081640 A2 | 3/2001 |
| WO | WO 2009/124838 A2 | 10/2009 |

OTHER PUBLICATIONS

English translation of International Search Report for PCT/EP2020/063332, mailed Sep. 10, 2020, 2 pages.

\* cited by examiner

OPHTHALMOLOGICAL IMPLANT AND METHOD FOR PRODUCING SAME

RELATED APPLICATIONS

This application is a National Phase entry of PCT Application No. PCT/EP2020/063332 filed May 13, 2020, which application claims the benefit of priority to DE Application No. 10 2019 207 175.9 filed, May 16, 2019, the entire disclosures of which are incorporated herein by reference.

TECHNICAL FIELD

The present invention relates to an ophthalmological implant which comprises an imaging optical element, in particular a central optical lens, and a haptic with a haptic root which adjoins the imaging optical element. Such an ophthalmological element is an intraocular lens, for example. The present invention furthermore relates to a corresponding method for producing an ophthalmological implant, in which the ophthalmological implant is formed by application of a machining lathing (and/or milling) method, a laser beam forming method or a primary forming method. Moreover, the invention relates to a characterization system for identifying an ophthalmological implant, for example an intraocular lens, to a computer program product and to a computer-readable medium.

BACKGROUND

Most ophthalmological implants, for example those produced from artificial materials, the majority of which are commercial intraocular lenses (IOL), are labeled by a label on the primary and secondary packaging. In addition to manufacturer information, it is possible to find, e.g., the type of intraocular lens and its dioptric power on the label. The correct treatment of the patient therefore assumes that the packaged and supplied intraocular lens, or another ophthalmological implant, corresponds in terms of its properties to the specifications on the labels of the packaging. In this context the user must rely on the manufacturer since an unambiguous identification or a check in the operating theater only on the basis of the visual lens features is difficult. Hence, there is the risk of mix-ups and incorrect labeling on the part of the manufacturer which, as a consequence, might lead to explantations in order then to implant, e.g., a new, correct intraocular lens into the patient. Consequently, the patient would be burdened multiple times. Moreover, mere speculation that a mix-up could have occurred leads to costly and reputation-damaging product recalls.

Therefore, methods have been proposed, for example in WO 2009/124838 A2, to mark the intraocular lenses with IR labels which are realized by the application of fluorescing dyes. A further known option for individual labeling lies in the application of laser-engraved matrix codes in the haptic according to DE 10 2009 056 810 A1, which is generated in an additional method following the generation of the ophthalmological implant. However, these methods are very complicated from a technical point of view and for example in the case of IR labeling require an additional biocompatible fluorescent dye and a complex fluorescence excitation and detection system. By contrast, marking the haptic by the laser-engraved matrix code requires a corresponding laser system and verification for biocompatibility of the method. All previously known methods have to be incorporated in the manufacturing chain in such a way that there is no possibility of incorrect labeling of the intraocular lens as a result of operating or programming errors. Since each of these are additional production steps in separate methods and with separate apparatuses in this case, a residual risk of mix-up nevertheless remains.

SUMMARY OF THE INVENTION

The present invention provides an unambiguous label with at least the type and the refractive power on an ophthalmological implant, in particular on an intraocular lens, and hence provides an unambiguous and reliable identification option without requiring additional additives, biocompatible materials, chemicals or novel production methods. The application of the label is positively driven, is not able to be mixed-up and is possible with minimal additional technical outlay.

An ophthalmological implant comprises an optically imaging optical element with a front side and a back side and a circumferential edge. This imaging optical element can and must be held on this circumferential edge of the imaging optical element (or at least in the direct vicinity thereof) since all other holding positions would restrict the optical usability of the element. For holding, stabilization, positioning or centration and fixation purposes at the point of application in a patient's eye, ophthalmological implants therefore moreover comprise a haptic with a haptic root which adjoins the imaging optical element, in particular at least partly encloses the latter at its circumferential edge and consequently provides a secure hold. Thus, as a rule, there is a secure connection between the imaging optical element and the haptic by way of the haptic root. In this case, the term haptic should include any body of such an ophthalmological implant that is situated peripherally with respect to the optical unit.

As a rule, the imaging optical element of the ophthalmological implant is a central optical lens. The latter is held by a haptic adjoining said lens at usually a plurality of positions of the circumferential edge.

As already mentioned above, the largest group of ophthalmological implants relates to intraocular lenses. These (just like most other ophthalmological implants) are produced from a biocompatible artificial material, as a rule a polymer, or any other organic material, but optionally also from a glass, in particular a silicate glass. Ophthalmological implants from the specific group of transplantations (which are usually also referred to as such) should not fall within the scope of the invention.

According to the invention, a structural code of identification data of the ophthalmological implant, for example of the type and of the refractive power, is now arranged on the haptic root and/or on the region of the haptic close to the haptic root.

In this case, a "structural code" is understood to mean a code with a structure having a topography, i.e., a code that is recognizable from its form, from its morphology. Very advantageously, such a "structural code" is generated in the same forming method as the ophthalmological implant that is to say as, in principle, an "in-situ structural code".

The identification data of the ophthalmological implant comprise the characterizing parameters of said ophthalmological implant, that is to say represent the label of the ophthalmological implant by which the latter can be unambiguously identified or verified. As mentioned above, this relates to the type of the ophthalmological implant, for example of an intraocular lens, and also all necessary information relating to optical properties like—in the case of the intraocular lens—its refractive power.

The arrangement on the haptic root or on the haptic close to the haptic root allows a reliable identification of the ophthalmological implant, for example of an intraocular lens, in various situations: It is easily recognizable and identifiable on the implant prior to implantation, but also still reachable for identifying, e.g., an intraocular lens following the implantation into the patient's eye if the latter is "dilated by eye drops" to this end.

In an example configuration of the ophthalmological implant according to the invention the structural code of the identification data of the ophthalmological implant, i.e., its labeling, is realized by application of a barcode system. A barcode system facilitates binary coding by use of very simple structures. Depending on the specific realization of the barcode system it allows storage and subsequent reading of a relatively large number of data, and so optionally further data such as production location, production process, date, etc. can also be stored within the meaning of an unambiguously understandable product label—in addition to the type of the ophthalmological implant and its optical data.

Now returning to the explanation of the general concept of the invention in greater detail: Ophthalmological implants, including intraocular lenses, have a certain rotational symmetry. The optically imaging element, as a rule an optical lens arranged as centrally as possible, is then surrounded at least in portions of its circumferential edge by a haptic with a haptic root, in which the structural code (within the meaning of a topographic code) is arranged in rotationally symmetric fashion on a haptic root and/or in the region of the haptic which is close to the haptic root and which partly encloses the optically imaging element at its circumferential edge. In this case, the rotational symmetry is interrupted at the points at which no haptic adjoins the circumferential edge of the lens.

Thus, for as long as the code is configured as a barcode, this relates to a ring-shaped barcode in principle, which is realized around the circumferential edge of the optically imaging element in the entire region of the haptic root and the region of the haptic close to the haptic root. If need be, the ring form is interrupted where the imaging optical element, in particular the intraocular lens, is not enclosed by a haptic. In this case, the most important information items—such as the type designation of the ophthalmological implant and the decisive optical properties such as for example the refractive power of a corresponding intraocular lens—are for example arranged closest to the imaging optical element.

In the case of such a rotationally symmetric embodiment of the structural code by way of a rotationally symmetric circular barcode (which is interrupted where no haptic is present), the ophthalmological implant according to the invention is realizable in particularly simple and reliable fashion: Both the forming of the ophthalmological implant and the structural coding can be implemented for example by use of one and the same machining lathing (and/or milling) method, in particular a diamond lathing (and/or milling) method, or else by a laser beam forming method (in which either the ophthalmological implant to be formed is rotated while the laser beam is guided over the lens along a radius of the lens or a rotational scan is realized including a displacement of the laser beam along a radius of the lens with a stationary ophthalmological implant to be formed). The rotationally symmetric barcode generated in this way facilitates a structural code of the ophthalmological implant which is arranged such that it is easily readable in various situations, in particular also following the implantation.

The structural code of the ophthalmological implant according to the invention is for example determined by a set of spatial modulation parameters of corresponding structures which are on the haptic root and the haptic and are used for coding.

An example ophthalmological implant according to the invention is characterized by a code which is described by at least one of the following modulation parameters: groove width, groove depth, inclination angle of the groove, position of the groove, in particular a radial position of the groove, described by the radius of the groove center of the respective groove for a rotationally symmetric code. In this case, groove refers to a depression, a notch or a "trench" created by various approaches in the material of the haptic root and the part of the haptic of the ophthalmological implant which is close to the haptic root. If the groove has not been introduced in perpendicular fashion the groove depth denotes the maximum depth of this groove, the groove width denotes the width of the groove at the upper edge, and a curvature of a groove wall can be a modulation parameter which is equivalent to an inclination angle of an angled but planar groove wall.

Thus, at least one corresponding spatial modulation parameter must be varied to store the desired data in the code. How many and which modulation parameters can be used for the structural code also depends on the optical detection method with which the spatial modulation parameter can be captured best, and whether and how such a detection method or a corresponding characterization system is available.

Depending on the configuration, at least working in binary is possible for the code. However, higher resolutions are also possible for the spatial compression of the data structure if, for example, it is not only possible to simply determine that a groove is present at a defined position, for example at a defined radius to the center of the optically imaging element, but also possible to detect different groove depths.

If such a compression of the data structure can be used it is possible to introduce further labels, redundancy bits, checksums or start-stop labels depending on the achievable spatial resolution of the data structure.

It is particularly advantageous if, ideally, the entire ophthalmological implant according to the invention has been manufactured from one workpiece, but at least if the optically imaging element and the haptic with its haptic root have been manufactured from one workpiece. As a rule, such an ophthalmological implant is worked out of a biocompatible polymer material for example, for example by way of a diamond lathing (and/or milling) method. However, as already mentioned, any machining lathing (and/or milling) method or a laser beam forming method can be used in this working out process. Alternatively for example, the ophthalmological implant can also be produced from a biocompatible polymer material by a primary forming method (casting, injection molding).

In this case, it is very advantageous if the structural code is formed during or directly after the forming of the ophthalmological implant in the case of an ophthalmological implant according to the invention. Then, forming and coding take place in one work step without the worked-on ophthalmological implant having to implement a change in location. Manufacturing data for the forming of the ophthalmological implant can then be used directly for coding.

In this case, the greatest possible reliability for a subsequent error-free identification of the ophthalmological implant is achieved.

In a method according to the invention for producing an ophthalmological implant, in particular an intraocular lens, the ophthalmological implant is formed by application of a machining lathing (and/or milling) method, in particular by application of a diamond lathing (and/or milling) method, and structural coding of identification data of the ophthalmological implant, for example of the type and of the refractive power, is implemented by application of the machining lathing (and/or milling) method (in particular by application of the diamond lathing (and/or milling) method if the latter is used) directly during or after the forming of the ophthalmological implant—for simple, reliable and unambiguous labeling of the implant. No machines have to be changed to this end; the ophthalmological implant remains in its place. To this end, the diamond lathing (and/or milling) method is a particularly suitable method for producing an ophthalmological implant, in particular an intraocular lens. However, other machining lathing (and/or milling) methods can also be used, for example the precision lathing (and/or milling) method.

In an alternative method according to the invention for producing an ophthalmological implant, in particular an intraocular lens, the ophthalmological implant is formed by application of a laser beam forming method. In this case, too, the structural coding of identification data of the ophthalmological implant is implemented during or after the forming of the ophthalmological implant using the same method, that is to say the laser beam forming method in this case. Within the scope of such a laser beam forming method, either the ophthalmological implant to be formed is rotated while the laser beam is guided over the lens along a radius of the lens or a rotation scan of the laser beam is realized, including the displacement of the laser beam along a radius of the lens with a stationary ophthalmological implant to be formed.

In this case, too, this structural code from the laser beam forming method comprises, in particular, the type and the refractive power for simple, reliable and unambiguous labeling of the implant. No machines have to be changed to this end in this case either; the ophthalmological implant remains in its place.

Such a laser beam forming method can operate using a laser which removes material by ablation, for example an excimer laser or an IR laser. However, this may also operate using a laser which "cuts" the material or removes the material at the point of the focusing effect on or in said material by application of photodisruption, for example a femtosecond laser or a picosecond laser (that is to say, very generally, a pulsed laser). In both cases, a corresponding laser system which is intended to carry out such a laser beam forming method requires a scanner which moves the focus of the laser beam on or in the material in all three spatial directions (or at least in the two spatial directions perpendicular to the optical axis or the propagation direction of the laser beam in the case of an ablation laser), in accordance with a pattern that has been specified for the desired forming.

As a rule, structural coding of identification data of the ophthalmological implant is implemented tightly next to the imaging optical element of the ophthalmological implant on its haptic, in particular on its haptic root, so that the optical function of the ophthalmological implant is not impaired but it is possible to identify the ophthalmological implant in many positions, optionally even after its implantation in a patient's eye.

Thus, according to the invention, the structural coding of identification data of the ophthalmological implant is implemented using the same method as the forming of the ophthalmological implant—following the forming or even already during the forming of the ophthalmological implant. The location of the ophthalmological implant is not changed, removing the risk of ophthalmological implants being changed or mixed-up, as would occur, for example, in the case of a manipulation of the ophthalmological implant between a forming method and a separate coding method.

For intraocular lenses as the most important group of ophthalmological implants, for example, a rotationally symmetric structural code is introduced in a region of the haptic root of the intraocular lens, and hence in the direct vicinity of the central optical lens, by application of a diamond lathing (and/or milling) method that exists for the production of said lenses or else by application of any of the machining lathing (and/or milling) methods.

In a particularly advantageous example variant of the method according to the invention, data, in particular control data (for example for the diamond lathing (and/or milling) method or any other machining lathing (and/or milling) method, or a laser beam forming method), for carrying out the structural coding of identification data of the ophthalmological implant are obtained from control data for forming the ophthalmological implant and/or from monitoring data of the forming of the ophthalmological implant.

In this case, the control data for forming the ophthalmological implant are the data for direct control of a corresponding lathing (and/or milling) machine, like the data from a CNC file. Monitoring data are data from feedback of the lathing (and/or milling) machine, for example the feedback of the relative position of the diamond or of any other machining tool (as a function of location and time) during grinding.

The information for the machine control for the so-called contour cut (i.e., the forming of the ophthalmological implant) are fixedly stored in terms of the data structure in the respective CNC file of the ophthalmological implant, in this case preferably of the intraocular lens with the corresponding dioptric power and type. Thus, upon application of the method according to the invention, each ophthalmological implant, in particular each corresponding intraocular lens, produced by use of one of the CNC files created and labeled in advance necessarily and directly contains the topographic label structure that fits thereto, that is to say the corresponding structural code (e.g., Type ABCD @ 20.0 dpt). A mix-up is precluded by this forced coupling. By way of this label, the ophthalmological implant, that is to say the intraocular lens for example, is labeled unambiguously, at least in terms of type and dioptric power in the case of an IOL, once the model-defining forming on the lathing (and/or milling) machine has taken place. Thus, the data labeling the ophthalmological implant, such as type and dioptric power of an intraocular lens, can be unambiguously ascertained and compared to the documentation or labeling at all necessary points in the production process, packaging process, delivery process, prior to and during an operation, and optionally even following an implantation in a patient's eye.

Alternatively—if a laser beam forming method is used—the control data for forming the ophthalmological implant are data for the spatial control of the laser focus (i.e., control data of the scanner of a laser system) and data for controlling the power and optionally the pulse duration of the laser. In this case, monitoring data can be, for example, feedback data from the scanner or the laser or else data from an additional characterization apparatus integrated in the laser system, by use of which the forming of the ophthalmological implant by application of the laser system can be characterized directly.

In a further alternative method according to the invention for producing an ophthalmological implant, for example an intraocular lens, the ophthalmological implant is formed by use of a primary forming method, within the scope of which there is a forming transfer of the desired form of the ophthalmological implant from a primary mold, and structural and rotationally symmetric coding of identification data of the ophthalmological implant, in particular of the type and of the refractive power, is implemented by the primary mold directly during the forming of the ophthalmological implant—for the simple, reliable and unambiguous labeling of the implant. Once again, there is no need to change machines to this end; forming and coding are implemented in the same method. In this case, the primary mold already contains the necessary structural and rotationally symmetric code of identification data of the ophthalmological implant, in particular of the type and of the refractive power, for the forming transfer to the implant as a negative of the structural coding then provided on the ophthalmological implant. An example primary forming method to this end is the injection molding method. However, the method of polymerization in the primary mold or any other casting method can be used.

In this case, too, structural coding of identification data of the ophthalmological implant is for example implemented tightly next to the optically imaging element of the ophthalmological implant on its haptic, in particular on its haptic root, so that the optical function of the ophthalmological implant is not impaired but it is possible to identify the ophthalmological implant in many positions, optionally even after its implantation in a patient's eye, for the purposes of which a rotationally symmetric structural code is particularly suitable.

For intraocular lenses as the most important group of ophthalmological implants, a rotationally symmetric structural code is introduced in a region of the haptic root of the intraocular lens, and hence in the direct vicinity of the central optical lens, by use of the primary forming method that exists for the production of said lenses.

If a primary forming method is used for producing an ophthalmological implant without there being post-processing of the ophthalmological implant, then it is furthermore particularly advantageous, for example, if the data for carrying out the structural coding of identification data of the ophthalmological implant are obtained from control data for creating a primary mold for forming the ophthalmological data and/or from monitoring data of the creation of the primary mold for forming the ophthalmological implant and said data are deposited (as a negative) in the primary mold during or directly after the creation of the primary mold, for example by use of a lathing (and/or milling) method or laser beam forming method, within the scope of the same method.

A further option for producing an ophthalmological implant consists in a combination of a primary forming method, for example an injection molding method, by use of which a general form of the ophthalmological implant is generated using a general primary mold. Subsequently, a lathing (and/or milling) method or a laser beam forming method as described above can be used very effectively in order to transfer the desired specific (optical) properties to the ophthalmological implant with corresponding fine forming, and also to carry out, directly during this method step, rotationally symmetric structural coding that describes these properties.

A characterization system according to the invention for identifying an above-described ophthalmological implant, for example an intraocular lens, comprises an illumination system for illuminating a structural code, a camera system for recording structures of the structural code rendered detectable by use of the illumination, and an analysis unit for evaluating an image, recorded by the camera system, of the structures of the structural code rendered detectable by use of the illumination and for decoding identification data for identifying the ophthalmological implant from said image.

In this case, neither the illumination system nor the camera system requires a special embodiment, a large number of conventional illumination systems and camera systems are usable to this end. However, camera system and illumination system should be matched to one another such that the light of the illumination system is readily detectable by the camera system. Actually, all that is required in that case is an additional analysis unit which facilitates an image analysis of an image recorded by use of the camera system and which is configured to decode this image and consequently "translate" the latter into freely legible specifications in relation to the properties of the ophthalmological implant.

An example characterization system according to the invention furthermore comprises a display and/or output apparatus for displaying and/or outputting the decoded identification data of the ophthalmological implant. The decoded identification data of the ophthalmological implant can be displayed directly to the user by way of a display apparatus. An output apparatus for example facilitates communication with other systems, too, that is to say is able to output or transmit the identification data to other systems. This can be implemented by way of wired or wireless communication paths. This also includes the option of storage on a storage medium for retrieval in other systems.

Particular preference, for example, is given to a characterization system in which the display and/or output apparatus, for example in conjunction with the analysis unit, is configured
- to further process the identification data of the ophthalmological implant and/or
- to store the identification data in an external database and/or
- to compare the identification data to data from an external database and/or
- to provide feedback (such as alarms, warnings or confirmations, for example) to a user.

By way of example, such a database can be a practice management system, an electronic patient file or a general implant database. The latter also includes a central external implant database system for registration and long-term or even time-unlimited tracing of implants.

In the case of a comparison of the identification data with an external database it is thus possible for example to compare the correspondence of the identified ophthalmological implant with an entry in the patient's file. In the case of a non-correspondence, suitable countermeasures (or alarms) can be initiated immediately at this point, and so an implantation of an incorrect ophthalmological implant in a patient's eye can be prevented at various points up to the operation itself.

In a variant of the characterization system according to the invention, the illumination system is designed as a slit illumination system which represents a simple type of illuminating and rendering detectable such a structural code.

A characterization system according to the invention in which the illumination system and camera system are designed to operate with light in the non-visible range, for example, is particularly advantageous. By way of example, it is possible to avoid the patient's eye being blinded using an illumination system and a camera system which operates in the near-infrared range, but also with light of other non-visible wavelengths. In this case, it is not necessary to simultaneously illuminate and read the entire rotationally symmetric structural code: Rather, it is sufficient to illuminate a small region of this code in such a way that along a radius of the code the latter can be fully illuminated and hence it is possible to capture all of the information which of course is situated in this radial region at each point of the haptic (and the haptic root in particular). Hence, the situation is very convenient since it is no longer necessary to search for the information at a very precise point which, for example post-implantation risks of being no longer accessible; instead, it is possible to simply choose a region in which accessibility is a given.

A microscopy system according to the invention, for example a surgical microscopy system, contains an above-described characterization system such that the system can be used for monitoring or tracking the implantation of an above-described ophthalmological implant, as is usual, and the identification data of the ophthalmological implant can additionally be decoded. For example, the decoded identification data of the ophthalmological implant can moreover be superimposed into a microscope image plane or into the observation beam path of the microscope in the case of such a microscopy system. Hence, in addition to the usual information from the observation of the course of the operation, the user always has knowledge of the identification data of the ophthalmological implant just to be implanted:

Hence, it is always possible to read the data structure, for example at a surgical microscope. Thus, if in doubt, the user (as a rule the surgeon) can check the type and the optical data of the ophthalmological implant, for example type and dioptric power of an intraocular lens, at all times during the operation or in the case of the complaint.

Furthermore, it is advantageous, for example, if a microscopy system according to the invention is furthermore configured to evaluate the image recorded by the camera system for the purposes of recognizing changes in relative position and absolute position of the ophthalmological implant during an implantation into a patient's eye: The structural code is very well suited to track a change in position, possibly even an involuntary change in position, of the implant and hence—in addition to the identification of the ophthalmological implant—has an additional use or provides an additional safety aspect.

Ideally, the evaluation of the data structure of the structural code and the representation of the clear data are implemented by a characterization system with a digital camera system. As described herein, the latter can be coupled to a visual observation microscope or else be arranged in a specific testing means.

A computer program product according to the invention contains program code which, upon execution on a computer, generates data, in particular control data for a processing machine, to carry out the structural coding of identification data of an ophthalmological implant or to deposit the structural coding in a primary mold, said data being generated from control data for a processing machine for forming the ophthalmological implant and/or from monitoring data of the forming of an ophthalmological implant, in particular by use of a machining lathing (and/or milling) method or a laser beam forming method, or from control data for a processing machine for forming a primary mold and/or from monitoring data of the forming of said primary mold for the production of an ophthalmological implant.

Such an ophthalmological implant for which data for structural coding can be generated with the aid of the computer program product is an intraocular lens, in particular.

In this case, the computer on which the computer program product can be executed can also be part of a control unit of a lathing (and/or milling) machine or a laser system.

The computer on which the computer program product can be executed can alternatively also be part of a control unit of a processing machine for producing a primary mold.

In particular, the computer program product can be configured for example to calculate a modulation structure for the structural code corresponding to the lens type and the refractive power and preferably to immediately convert this into control data for the generation thereof from the numerical lens type label and the dioptric power of an intraocular lens currently in production by use of a machining lathing (and/or milling) method or a laser beam forming method. By way of example, these control data can control the groove depth, groove width or inclination angle of the groove in the CNC file of a lathing (and/or milling) method.

If a primary mold is used to produce an ophthalmological implant, the computer program product can, by contrast, be configured in particular to calculate a modulation structure for the rotationally symmetric structural code corresponding to the lens type and the refractive power and preferably to immediately convert this into control data for the generation thereof from the numerical lens type label and the dioptric power of a primary mold for an intraocular lens currently in production. Using these control data it is also possible here to control, e.g., the groove depth, groove width or the inclination angle of the groove in the CNC file if the primary mold is produced by use of a lathing (and/or milling) method, for example. The above-described computer program product is stored on a computer-readable medium according to the invention.

BRIEF DESCRIPTION OF THE DRAWINGS

The present invention will now be explained on the basis of exemplary embodiments. In the drawings.

DETAILED DESCRIPTION

Figure 1A:
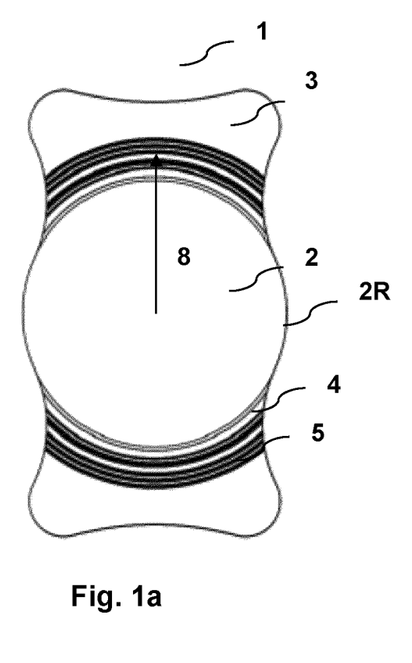
FIG. 1a depicts a first exemplary embodiment of an ophthalmological implant according to the invention with a structural code.

FIG. 1a illustrates a first example embodiment of an ophthalmological implant 1 according to the invention with a structural code 5. This ophthalmological implant 1 is an intraocular lens, comprising a central optical lens 2, which represents the optically imaging element of this ophthalmological implant 1, and a haptic 3 with a haptic root 4, which adjoins the central optical lens 2 along a portion of the circumferential edge 2R of said central optical lens 2, and which partially surrounds the latter on two sides in the process. A structural code 5 of identification data for the ophthalmological implant 1 is arranged on the haptic root 4 and the region of the haptic 3 close to the haptic root 4 of this intraocular lens. Here, this case relates to the structural code 5 of the type and the refractive power of this intraocular lens. In this case, use has been made of a structural code 5 in the form of a barcode system, which is arranged in a rotationally symmetric manner around the central optical lens 2 on the haptic root 4 and on the haptic 3 in the direct vicinity of the central optical lens 2. The structural coding 5 carried out here by grooves generated using the same diamond lathing (and/or milling) method in the same diamond lathing (and/or milling) machine, either directly in or following the forming process of the intraocular lens, uses a 2-bit solution: Grooves are generated (groove depth 7 "1") or no grooves are generated (groove depth 7 "0") at different radial positions, in each case with a fixed groove width 6.

Thus, this case sees a restriction to a few modulation parameters: The radial position of the groove with in each case the same groove width 6, at which the state of 1 or 0 is possible in each case. Therefore, such a binary structural code 5 is generable and also readable again using very simple means since all that needs to be determined is whether or not a groove is present at the respective radial position 8.

Figures 1B, 1C:
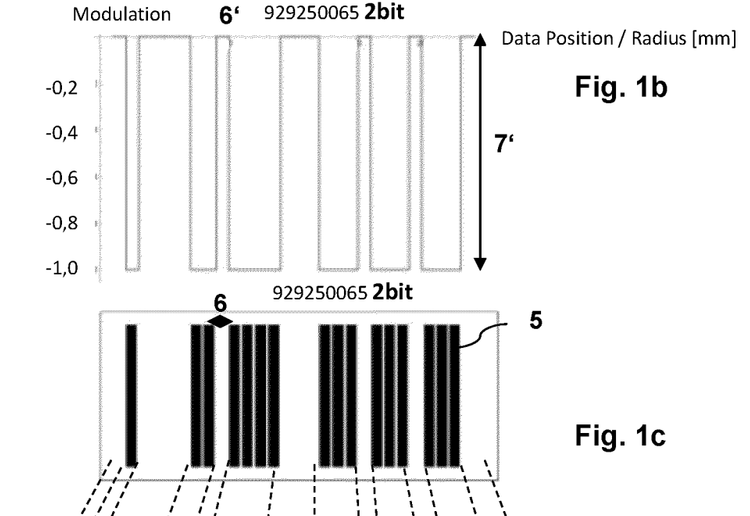
FIG. 1b depicts the corresponding state diagram of the structural code thereof.
FIG. 1c depicts a basic view of this structural code from above.
Figure 1D:
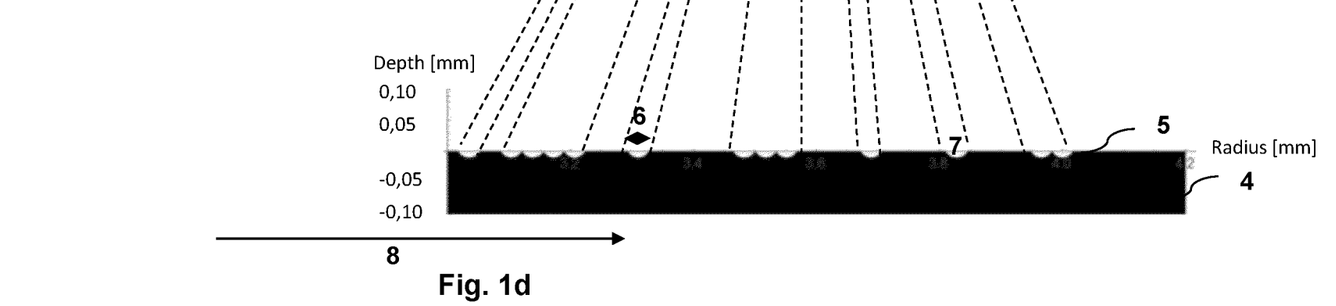
FIG. 1d depicts a section through the structural code of this implant.

Then, FIG. 1b shows the corresponding state diagram of the structural code 5 of this first example embodiment of the ophthalmological implant 1 according to the invention, i.e., of the first intraocular lens, in which the above-described two states are possible. FIG. 1c shows a basic view of this structural code 5 from above and FIG. 1d shows a section through the structural code 5 of this implant 1. Dashed lines were used to assign the same regions to one another.

Specifically, this first example embodiment illustrates a 2-bit code, which extends over a spatial width of approximately 1.0 mm. A pure depth modulation of the groove depth 7 for generating the two states 0 and 1 would be realizable, for example, with an amplitude of 5 μm-15 μm in the case of a tool radius of 10 μm.

If the structural code 5 generated with 2-bit coding in this first example embodiment is then decoded, the identification data for labeling this intraocular lens become apparent: This is an AT LARA toric 929 with a refractive power of SE=25 dpt and a cylinder correction of CYL=6.5 dpt.

Figure 2A:
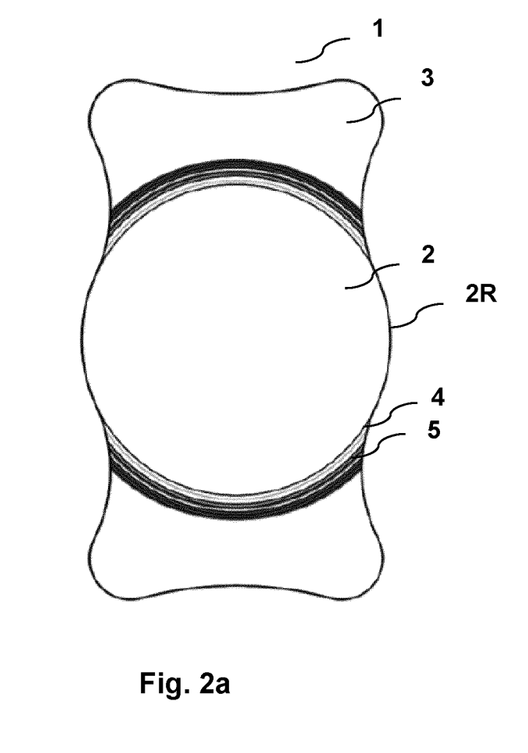
FIG. 2a depicts a second exemplary embodiment of an ophthalmological implant according to the invention with a structural code.

FIG. 2a illustrates a second example embodiment of an ophthalmological implant 1 according to the invention with a structural code 5. Once again this is an intraocular lens, specifically of the same type and with the same refractive power, but with a structural code 5 which contains further modulation parameters and therefore allows spatial compression of the data structure: In this case, there is an additional modulation of the groove depth 7 over a plurality of levels 7'-1, 7'-2, 7'-3. As is evident from this second example embodiment, the same amount of data only still requires about half the spatial width when such a 4-bit code is used.

However, for decoding this, a higher resolution of a corresponding characterization system 10 is required for the purposes of identifying this intraocular lens than for decoding the first example embodiment: A depth resolution of the groove depth such that the different levels 7'-1, 7'-2, 7'-3 can be distinguished from one another is required in this case.

If the structural code 5 generated with 4-bit coding in this second example embodiment is then decoded, the identification data for labeling this intraocular lens also become apparent in this case. Here, too, this is an AT LARA toric 929 with a refractive power of SE=25 dpt and a cylinder correction of CYL=6.5 dpt.

As already described above, the modulation parameters can also still comprise, e.g., the groove width 6 and/or the inclination angle of the groove in addition to the above-described radial position 8 of the grooves and the groove depth 7 in order to further compress the structural code 5 and house the same identification data in even less spatial width, or else in order to house substantially more information, i.e., additional identification data, over the same spatial width. What can be used here as a modulation parameter depends on what optical detection method and what characterization system 10 can be worked with and consequently whether the corresponding modulation parameter can be captured therewith.

Figure 2B:
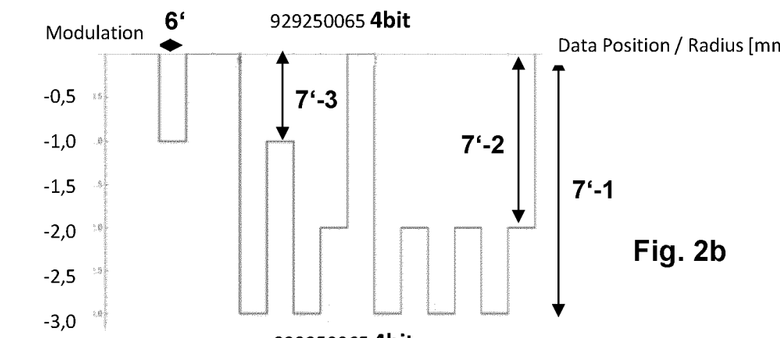
FIG. 2b depicts the corresponding state diagram of the structural code thereof.
Figure 2C:
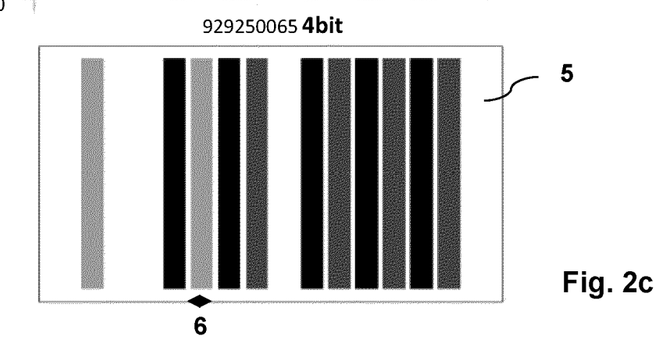
FIG. 2c depicts a basic view of this structural code from above.

Then, FIG. 2b shows the corresponding state diagram of the structural code 5 of this second example embodiment of the ophthalmological implant 1 according to the invention, i.e., of the second intraocular lens, in which the above-described four states (four different depths) are possible. FIG. 2c shows a basic view of this structural code 5 from above.

Figure 3:
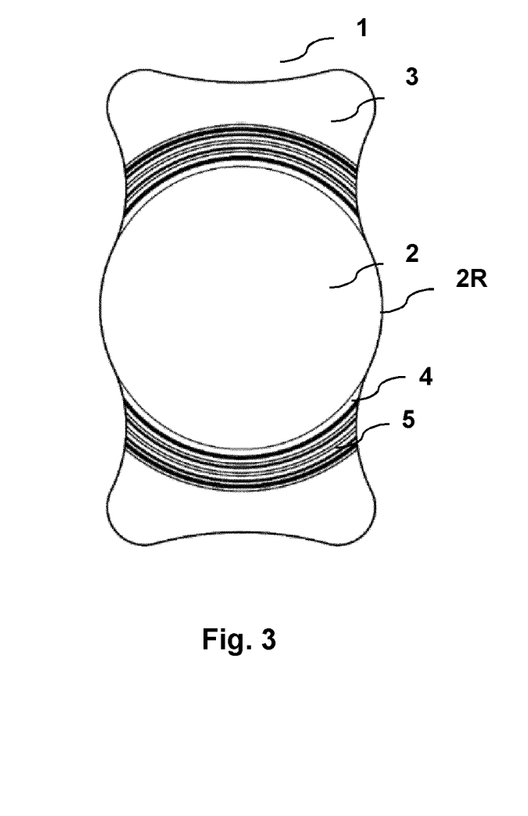
FIG. 3 depicts a third exemplary embodiment of an ophthalmological implant according to the invention with a structural code.

FIG. 3 illustrates a third ophthalmological implant 1 according to the invention with a structural code 5; this is an intraocular lens of the type AT LISA tri 809 with a refractive power of 25.0 dpt.

Figure 4:
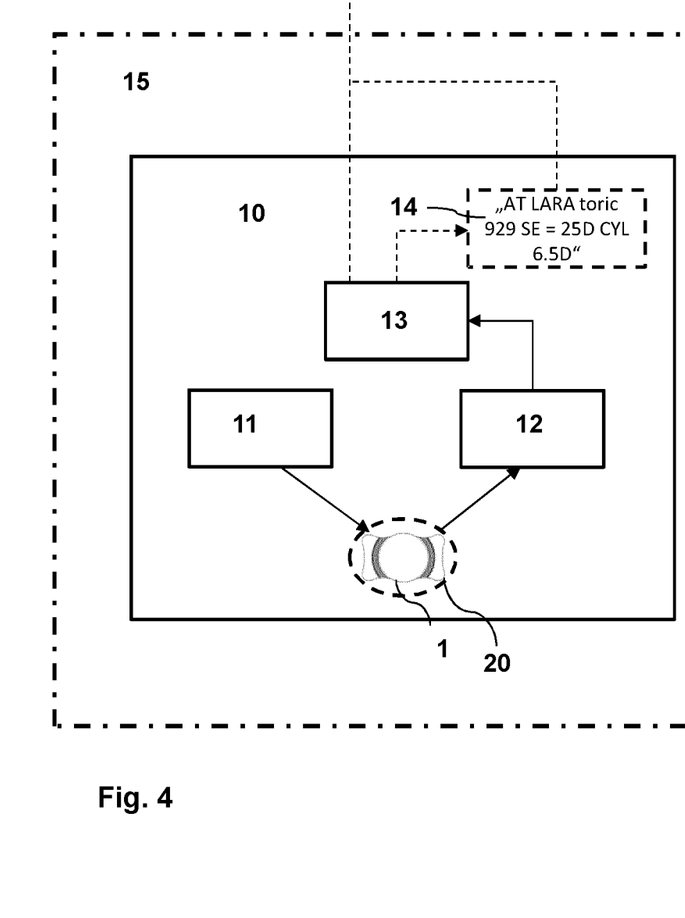
FIG. 4 depicts a characterization system according to the invention, which is part of a corresponding microscopy system.

Finally, FIG. 4 shows a characterization system 10 according to the invention for identifying an ophthalmological implant 1, in particular an intraocular lens, said characterization system being part of a corresponding microscopy system 15.

This example embodiment of a characterization system 10 according to the invention comprises an illumination system 11 for illuminating a structural code 5 of an intraocular lens, a camera system 12 for recording structures of the structural code 5 of the intraocular lens which have been rendered detectable by application of the illumination, an analysis unit 13 for evaluating an image, recorded by the camera system 12, of the structures of the structural code 5 rendered detectable by use of the illumination and for decoding of identification data for identifying the ophthalmological implant 1 from this image, and also a display and/or output apparatus 14 for displaying and/or outputting the decoded identification data of the ophthalmological implant 1.

In this case, this example embodiment of the characterization system 10 according to the invention can also decode intraocular lenses which have already been implanted in a patient's eye 20.

In this case, the aforementioned features of the invention, which are explained in various example embodiments, can be used not only in the combinations specified in an example manner but also in other combinations or on their own, without departing from the scope of the present invention.

A description of an apparatus relating to method features is analogously applicable to the corresponding method with respect to these features, while method features correspondingly represent functional features of the apparatus described.

The invention claimed is:
1. An ophthalmological implant, comprising:
   an imaging optical element;

a haptic with a haptic root which adjoins the imaging optical element;

wherein the haptic root at least partly encloses the imaging optical element at a circumferential edge of the imaging optical element; and a rotationally symmetric structural code of identification data of the ophthalmological implant arranged on the haptic root and/or on a region of the haptic proximate the haptic root;

wherein the rotationally symmetric structural code is symmetrical about a center of the imaging optical element and encodes the identification data of the ophthalmological implant by a ring shaped bar code.

2. The ophthalmological implant as claimed in claim 1, wherein the imaging optical element comprises a central optical lens and the identification data comprises a type and a refractive power of the ophthalmological implant.

3. The ophthalmological implant as claimed in claim 1, wherein the rotationally symmetric structural code encodes the identification data of the ophthalmological implant by a barcode system.

4. The ophthalmological implant as claimed in claim 1, wherein the rotationally symmetric structural code is generated by lathing and/or milling, a diamond lathing and/or milling method, or a laser beam forming method directly during or after the forming of the ophthalmological implant.

5. The ophthalmological implant as claimed in claim 1, wherein the rotationally symmetric structural code is determined by a set of spatial modulation parameters.

6. The ophthalmological implant as claimed in claim 5, wherein the rotationally symmetric structural code is described by at least one of the following modulation parameters: groove width, groove depth, inclination angle of the groove, position of the groove, or a radial position of the groove.

7. The ophthalmological implant as claimed in claim 1, wherein the imaging optical element and the haptic including the haptic root are a unitary structure.

8. The ophthalmological implant as claimed in claim 1, wherein the rotationally symmetric structural code is formed during or directly after the forming of the ophthalmological implant.

9. A method of producing an ophthalmological implant, comprising:

forming the ophthalmological implant by machining, lathing and/or milling or by a laser beam forming method;

forming an imaging optical element;

forming a haptic with a haptic root which adjoins the imaging optical element;

forming the haptic root so that the haptic root at least partly encloses the imaging optical element at a circumferential edge of the imaging optical element; and forming a rotationally symmetric structural coding of identification data of the ophthalmological implant arranged on the haptic root and/or on a region of the haptic proximate the haptic root by application of the machining, lathing and/or milling or the laser beam forming method directly during or after the forming of the ophthalmological implant; and forming the rotationally symmetric structural code to be symmetrical about a center of the imaging optical element and to encode the identification data of the ophthalmological implant by a ring shaped bar code.

10. The method as claimed in claim 9, wherein the machining, lathing and/or milling further comprises forming the ophthalmological implant by diamond lathing and/or milling.

11. The method as claimed in claim 9, further comprising encoding a type and a refractive power in the rotationally symmetric structural coding of identification data.

12. The method as claimed in claim 9, wherein the ophthalmological implant comprises an intraocular lens.

13. The method as claimed in claim 9, further comprising obtaining data, including control data, for carrying out the rotationally symmetric structural coding of identification data of the ophthalmological implant from control data for forming the ophthalmological implant and/or from monitoring data of the forming of the ophthalmological implant.

* * * * *

UNITED STATES PATENT AND TRADEMARK OFFICE
CERTIFICATE OF CORRECTION

| | | |
|---|---|---|
| PATENT NO. | : 12,419,737 B2 | Page 1 of 1 |
| APPLICATION NO. | : 17/610639 | |
| DATED | : September 23, 2025 | |
| INVENTOR(S) | : Mario Gerlach et al. | |

It is certified that error appears in the above-identified patent and that said Letters Patent is hereby corrected as shown below:

On the Title Page

Item (72), under "Inventor", Column 1, Line 1, delete "Glienicke-Nordbahn" and insert --Glienicke/Nordbahn--

In the Specification

Column 11, Line 26, delete "with in" and insert --within--

Column 11, Line 58, delete "structure:" and insert --structure.--

In the Claims

Column 14, Line 13, delete "element; and" and insert --element;--

Signed and Sealed this
Thirtieth Day of December, 2025

John A. Squires
*Director of the United States Patent and Trademark Office*